United States Patent
Sohrab

(10) Patent No.: US 7,343,188 B2
(45) Date of Patent: Mar. 11, 2008

(54) DEVICES AND METHODS FOR ACCESSING AND ANALYZING PHYSIOLOGICAL FLUID

(75) Inventor: Borzu Sohrab, Los Altos, CA (US)

(73) Assignee: Lifescan, Inc., Milpitas, CA (US)

( * ) Notice: Subject to any disclaimer, the term of this patent is extended or adjusted under 35 U.S.C. 154(b) by 537 days.

(21) Appl. No.: 10/143,253

(22) Filed: May 9, 2002

(65) Prior Publication Data

US 2003/0212347 A1    Nov. 13, 2003

(51) Int. Cl.
*A61B 5/05* (2006.01)

(52) U.S. Cl. .................. 600/345; 600/347; 600/365

(58) Field of Classification Search ........ 600/345–350, 600/583–584, 367–368, 371, 566; 204/403.1–415
See application file for complete search history.

(56) References Cited

U.S. PATENT DOCUMENTS

| | | | |
|---|---|---|---|
| 3,589,557 A | | 6/1971 | Johnson |
| 4,187,077 A | | 2/1980 | Covington et al. |
| 4,823,806 A | * | 4/1989 | Bajada .................... 600/557 |
| 5,510,266 A | | 4/1996 | Bonner et al. |
| 5,575,403 A | | 11/1996 | Charlton et al. |
| 5,660,791 A | | 8/1997 | Brenneman et al. |
| 5,759,010 A | | 6/1998 | Jacobs et al. |
| 5,797,693 A | | 8/1998 | Jaeger |
| 5,863,800 A | | 1/1999 | Eikmeier et al. |
| 5,971,941 A | | 10/1999 | Simons et al. |
| 6,093,156 A | | 7/2000 | Cunningham et al. |
| 6,228,100 B1 | | 5/2001 | Schraga |
| 6,472,220 B1 | | 10/2002 | Simons et al. |
| 6,530,892 B1 | * | 3/2003 | Kelly ..................... 600/583 |
| 6,540,675 B2 | | 4/2003 | Aceti et al. |
| 6,612,111 B1 | * | 9/2003 | Hodges et al. ............ 60/583 |
| 6,706,159 B2 | * | 3/2004 | Moerman et al. ...... 204/403.03 |
| 2002/0137998 A1 | * | 9/2002 | Smart et al. .............. 600/347 |
| 2004/0015063 A1 | * | 1/2004 | DeNuzzio et al. ........ 600/347 |

FOREIGN PATENT DOCUMENTS

| | | |
|---|---|---|
| DE | 198 19 407 A | 11/1999 |
| DE | 28 03 345 B | 7/2000 |
| EP | 0 985 376 A | 3/2000 |
| WO | WO01/23885 A1 | 4/2001 |
| WO | WO01/63272 A1 | 8/2001 |
| WO | WO01/64105 A1 | 9/2001 |
| WO | WO 01/72220 A1 | 10/2001 |
| WO | WO 02/49507 | 6/2002 |

* cited by examiner

*Primary Examiner*—Robert L. Nasser
(74) *Attorney, Agent, or Firm*—Wayne Jaeschke, Jr.

(57) ABSTRACT

Systems, devices and methods for determining the concentration of physiological fluid analytes are provided. The subject systems have a plurality of biosensor devices present on a disposable cartridge. Each biosensor device includes a biosensor and a skin penetration means. In practicing the subject methods, a movement means of the device is used to move each biosensor device in a first direction that provides for penetration of the skin-piercing means into a skin layer followed by movement of the biosensor in a second direction that provides for removal of the skin-piercing means from the skin layer, where this movement profile provides for physiological fluid access and analyte concentration determination by the analyte sensor means. The subject systems, devices and methods for using the same find use in determining the concentration of a variety of different physiological fluid analytes, and are particularly suited for use in detection of physiological fluid glucose concentration.

40 Claims, 12 Drawing Sheets

FIG. 1A
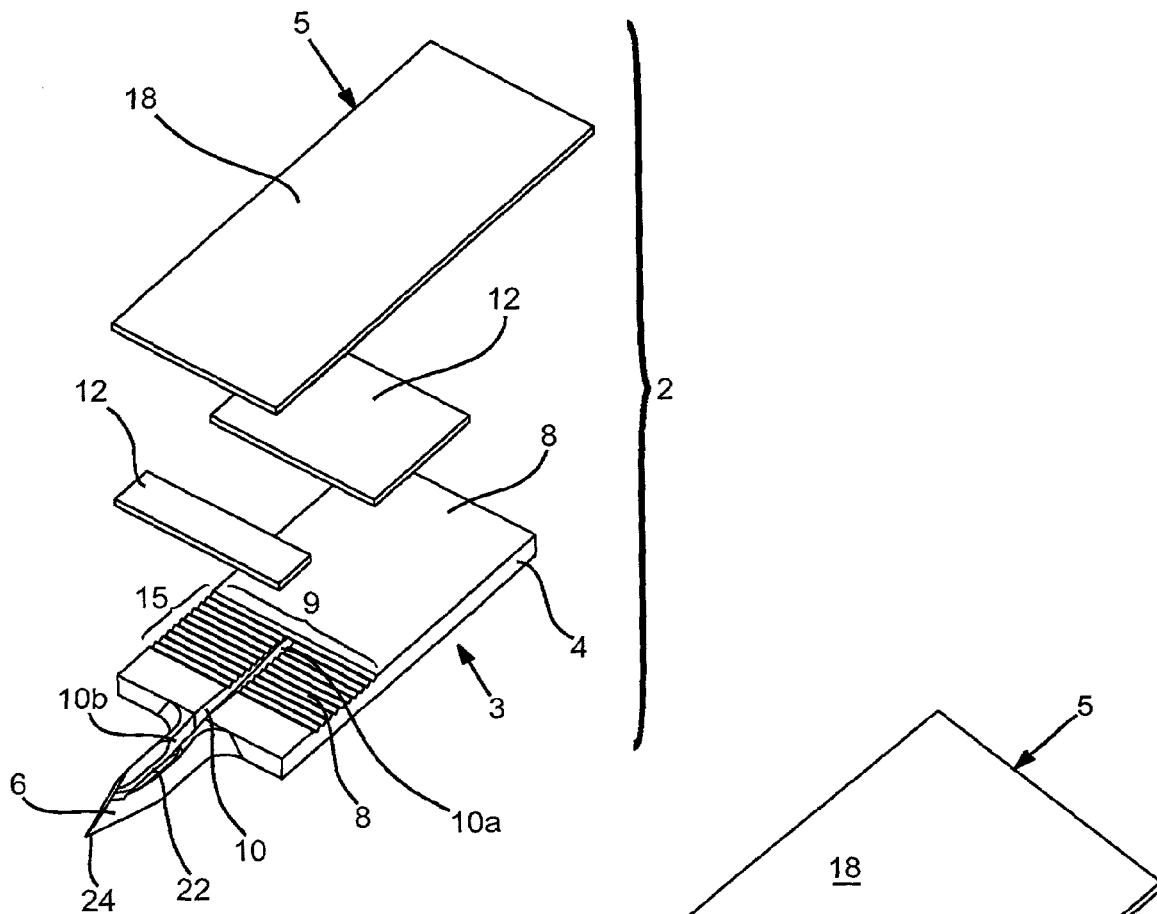
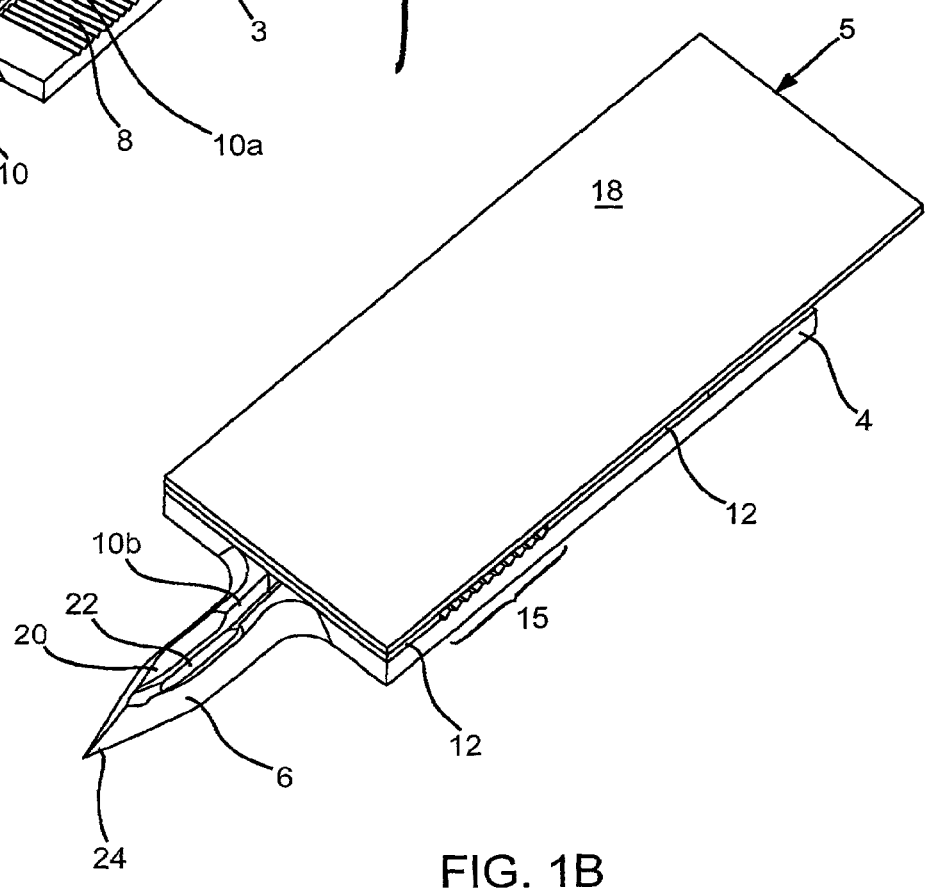
FIG. 1B

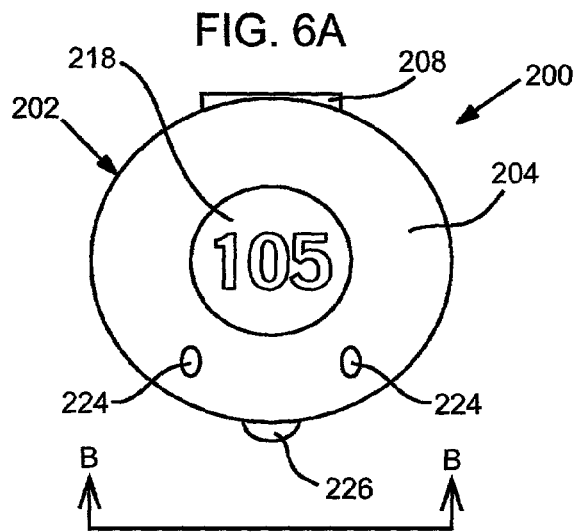
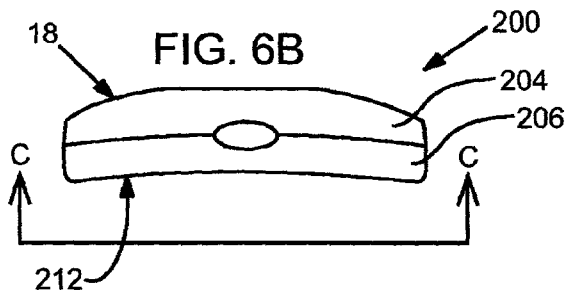
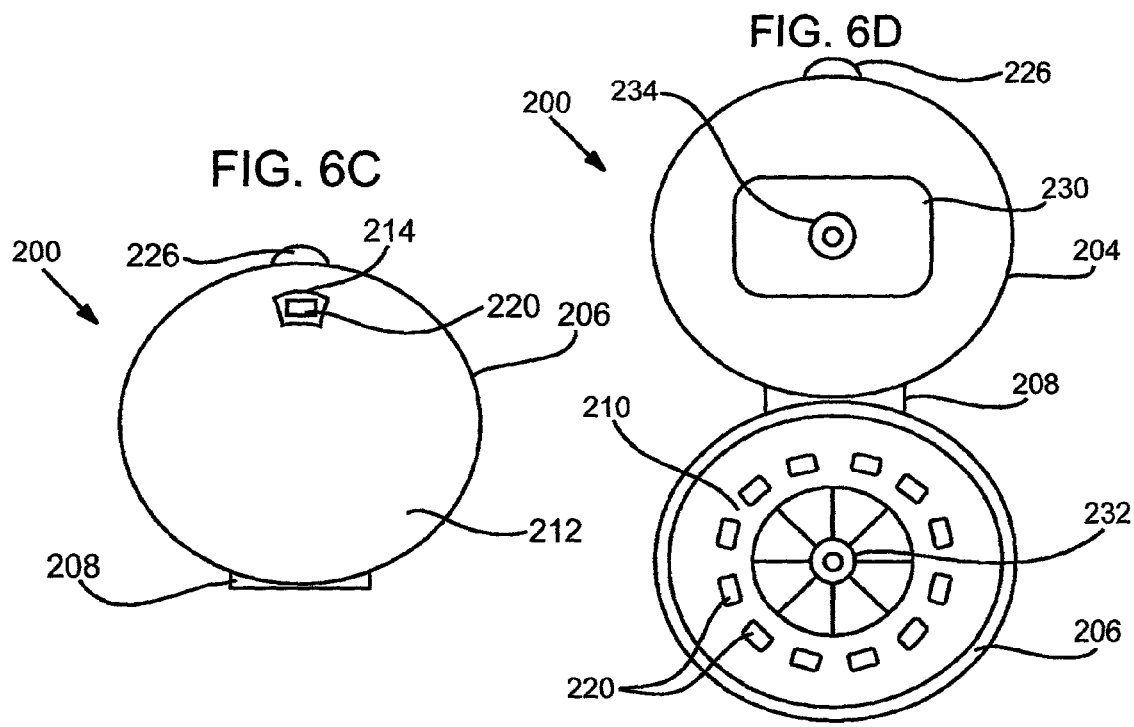

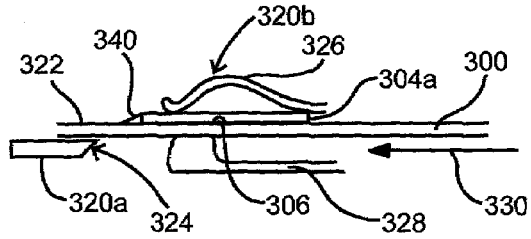
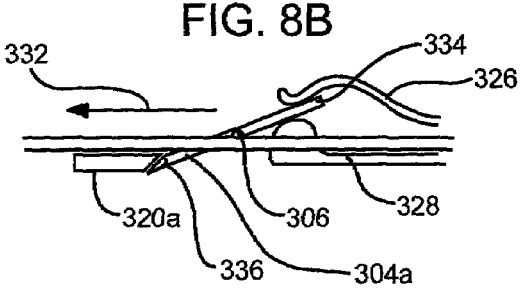
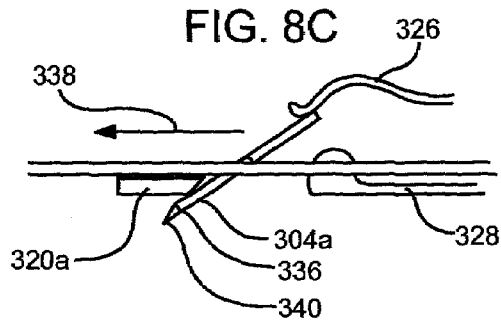
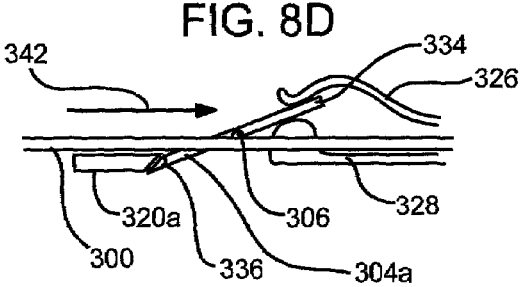
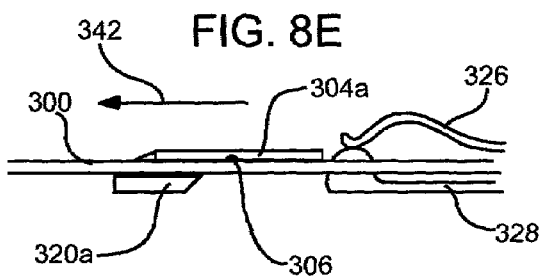
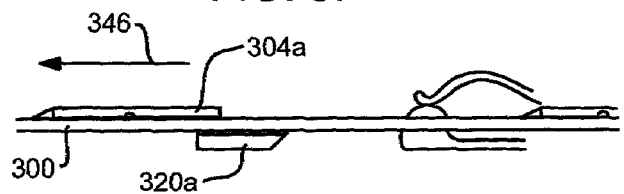

DEVICES AND METHODS FOR ACCESSING AND ANALYZING PHYSIOLOGICAL FLUID

FIELD OF THE INVENTION

The field of this invention is analyte concentration detection, particularly physiological fluid access and the determination of one or more analyte concentrations thereof.

BACKGROUND OF THE INVENTION

Analyte detection in physiological fluids, e.g., blood or blood derived products, physiological fluid, etc., is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

In determining the concentration of an analyte in a physiological sample, a physiological sample must first be obtained. Obtaining the sample often involves cumbersome and complicated devices which may not be easy to use or may be costly to manufacture. Furthermore, the procedure for obtaining the sample may be painful. For example, pain is often associated with the size of the needle used to obtain the physiological sample and the depth to which the needle is inserted. Depending on the analyte and the type of test employed, a relatively large, single needle or the like is often used to extract the requisite amount of sample.

The analyte concentration determination process may also involve a multitude of steps. First, a sample is accessed by use of a skin-piercing mechanism, e.g., a needle or lancet, which accessing may also involve the use of a sample collection mechanism, e.g., a capillary tube. Next, the sample must then be transferred to a testing device, e.g., a test strip or the like, and then oftentimes the test strip is then transferred to a measuring device such as a meter. Thus, the steps of accessing the sample, collecting the sample, transferring the sample to a biosensor, and measuring the analyte concentration in the sample are often performed as separate, consecutive steps with various device and instrumentation.

Because of these disadvantages, it is not uncommon for patients who require frequent monitoring of an analyte to simply become non-compliant in monitoring themselves. With diabetics, for example, the failure to measure their glucose level on a prescribed basis results in a lack of information necessary to properly control the level of glucose. Uncontrolled glucose levels can be very dangerous and even life threatening.

Advances have been made in analyte detection technology to overcome the disadvantages of the above described testing protocols. A primary advancement is the integration of the means for accessing physiological fluid and the means for testing the fluid for the presence and/or concentration of the analyte of interest, e.g., glucose. More specifically, such integrated devices include a biosensor having a skin-piercing element, such as a microneedle, integrated therewith. Such exemplary devices are disclosed in, for example, the following U.S. patent application Ser. No. 09/923,093; U.S. application Ser. No. 10/143,442, entitled "Physiological Sample Collection Devices and Methods of Using the Same" and filed on the same day herewith; U.S. application Ser. No. 10/143,129, entitled "Analyte Test Element with Molded Lancing Blade" and filed on the same day herewith; and U.S. application Ser. No. 10/143,127, entitled "Methods of Fabricating Physiological Sample Collection Devices" and filed on the same day herewith.

Despite such advancements, there is a continued interest in the development of new devices and methods for use in the determination of analyte concentrations in a physiological sample. Of particular interest would be the development of analyte concentration determination systems having integrated fluid accessing and testing functions, and methods of use thereof, that are automated in order to minimize manipulation by the user, convenient, easy and discrete to use, involve minimal pain, and enhance portability.

SUMMARY OF THE INVENTION

Systems, devices and methods for accessing physiological fluid and determining the concentration of one or more analytes thereof. The subject systems provide a cartridge device containing a plurality of single-use biosensor/skin-piercing/fluid access devices. The cartridge devices of the present invention have a flat or planar construct, and preferably have a disk shape but may have an elongated shape. The biosensor/skin-piercing/fluid access devices are provided within the cartridge in a serial configuration, preferably equally spaced from each other, parallel to a path along which the cartridge is caused to move or rotate. In disked shaped cartridges, such serial arrangement is about a circumference of the cartridge.

The subject systems further include a housing structure within which a cartridge is operatively loaded. The housing structure preferably has a skin-facing portion and/or surface which appositions a loaded cartridge loaded within to a section of the user's skin. The housing is preferably configured so as to be maintained against the skin for extended periods. To this end, the housing may have a "watchband" configuration to be worn on a limbic region, e.g., a wrist or forearm, of the user, or may have a configuration, such as a substantially planar configuration, for adhesive contact with a suitable location, e.g., torso, thigh, hip, etc., on the user's body.

Each biosensor/skin-piercing/fluid access device has a biosensor integrated with a skin-piercing or lancing element for piercing, cutting or lancing the skin and, in some embodiments, also includes a fluid collection channel or transfer pathway for transferring the sampled physiological fluid within the skin to the biosensor portion of the device. The biosensors may have an electrochemical, photometric or colorimetric configuration by which to perform a measurement on the sampled fluid. In some embodiments, the biosensor devices have a generally planar configuration wherein at least one skin-piercing member extends from the biosensor device. In certain of these embodiments, the skin-piercing member extends substantially within the same plane as the planar biosensor device, while in other embodiments, the skin-piercing member extends in a direction substantially transverse to the planar configuration of the biosensor device. More specifically, in some embodiments, the biosensor devices are configured as test strips wherein the skin-piercing element extends from a member or component, e.g., a substrate, an electrode or spacer layer, of the test strip. Certain other embodiments provide a frame member having a planar configuration having a biosensor pad or strip and a micro-lancing element mounted on and integrated to the same planar surface, but are spaced apart from each other to facilitate the function of that particular device. In still other embodiments, an angled structure is provided which extends distally into at least one microneedle formation and which supports a biosensor chamber at a proximal end thereof.

The subject systems further include a meter housed within the housing structure for analyzing the physiological fluid obtained by the biosensor/skin-piercing/fluid access devices. Connectors or contacts are provided to operatively couple the biosensor devices with the meter whereby the meter provides the requisite signals to the biosensor devices to perform the assay measurement and includes means for determining the value of such measurement.

The subject system further provides means for operatively moving, e.g., advancing and reversing, a subject cartridge relative to an aperture in the housing structure for exposing and concealing an individual biosensor/skin-piercing/fluid access device through the aperture to an access site on the user's skin. Alternately, at least a portion of the apertured housing structure is moveable to expose and unexposed an individual biosensor/skin-piercing/fluid access device. Such movement of the cartridge places the exposed biosensor devices in operative connection, via connectors and contacts, to the meter.

While the biosensor devices translate along with the cartridge device, in some embodiments, each biosensor device is operatively attached to the cartridge device so as to be movable relative to the cartridge device so as to optimize the angle by which the skin is to be pierced by the skin-piercing means, thereby reducing pain to the patient and trauma to the skin. Such movement involves deflection and/or rotation of a biosensor device about an axis which extends radially or perpendicular to the path through which the biosensors are caused to travel upon translation of the cartridge device. The movement of the biosensor devices relative to the cartridge is primarily accomplished passively such as by components fixed within the housing structure relative to the cartridge for advancing or deflecting each individual biosensor/skin-piercing/fluid access device through the housing aperture towards an access site on the user, penetrating the access site with the skin-piercing element and then withdrawing or retracting the device from the access site. Such components include but are not limited to ramp structures and clip mechanisms.

The subject systems may further include a controller, such as in the form of a microprocessor, for controlling the function of the meter and the movement of the cartridge and the biosensor devices, and for storing data related thereto. The controller is programmable whereby the assay protocol and the timing thereof may be customized according to software algorithms. Such algorithms provided for the "continuous" monitoring of concentration of an analyte in a user, i.e., for automatically measuring the concentration of an analyte in a user according to a predetermined scheduled, e.g., at two or more points over a given time period. The systems may also provide for the user to implement an assay "on demand," thereby overriding the continuous monitoring protocol. Such analyte concentration measurements are stored by the microprocessor or other memory storage means for immediate or later retrieval by the user or a physician. The subject systems may further include a display means for displaying the results of the assay and other relevant information. In certain embodiments, such systems include means for communicating with external devices for the transfer and receipt of information and data related to the assay results, the assay protocol, the user, the disposable cartridge, etc.

In practicing the subject methods, assay protocols are implement which involve accessing physiological fluid by piercing the user's skin with the skin-piercing element, collecting the accessed physiological fluid to within the biosensor and measuring the one or more target analytes within the physiological fluid. Each assay protocol involves the advancement or movement of the cartridge or an aperture associated therewith in a first direction that causes the skin-piercing element of an integrated biosensor device to penetrate the skin, followed by movement of the cartridge or aperture in a second direction that provides for removal of the skin-piercing element from the skin, where this movement profile provides for physiological fluid access and analyte concentration determination by the biosensor. Advancement of the cartridge or aperture may be performed manually by the user or driven by a motor controlled by the controller. Such advancement and skin-penetration may be done automatically according to a preprogrammed scheduled or at the will of the user.

The subject systems, devices and methods for using the same find use provide a repeatable fluid accessing and sampling interface between a biosensor and a target skin site for determining a chemical characteristic of the sampled fluid, typically, the concentration of a variety of different physiological fluid analytes, and most typically the concentration of glucose. The subject system and devices can be used in the continual measurement of an analyte of interest without the problems experienced with implantable analyte sensors. For example, because single-use substantially painless analyte measurement means are employed, user irritation and pain are avoided. Furthermore, the individual measurement means employed need not be calibrated prior to use. In addition, with respect to the glucose the subject devices and methods can not only be employed to rapidly and accurately detect the occurrence of a hypo or hyperglycemic event without host participation or intervention, but they can also be employed to readily predict the occurrence of hypo and hyperglycemic conditions, and therefore provide for improved management of blood glucose metabolism associated disease conditions. As such, the subject invention represents a significant contribution to the art.

These and other objects, advantages, and features of the invention will become apparent to those persons skilled in the art upon reading the details of the methods and systems of the present invention which are more fully described below.

BRIEF DESCRIPTION OF THE DRAWINGS

FIG. 1A is an exploded view of an embodiment of an electrochemical biosensor/skin-piercing/fluid access device suitable for use with the cartridge devices and systems of the present invention. FIG. 1B is a perspective view of the assembled device of FIG. 1A.

FIG. 6A is a top view of an embodiment of the system of the present invention having a user-friendly, portable configuration. FIG. 6B is a side view of the system of FIG. 6A taken along lines B—B. FIG. 6C is a bottom view of the systems of FIG. 6B taken along lines C—C. FIG. 6D illustrates the system of FIGS. 6A, 6B and 6C in an open condition, revealing a cartridge device of the present invention operatively positioned within the housing go the subject system.

FIGS. 8A to 8F provide a schematic representation of one embodiment of a biosensor movement means of a system of the present invention and the step-by-step movement of a biosensor/skin-piercing/fluid access device of FIGS. 1, 2 or 3 on a cartridge of the present invention.

DETAILED DESCRIPTION OF THE INVENTION

Figure 2A:
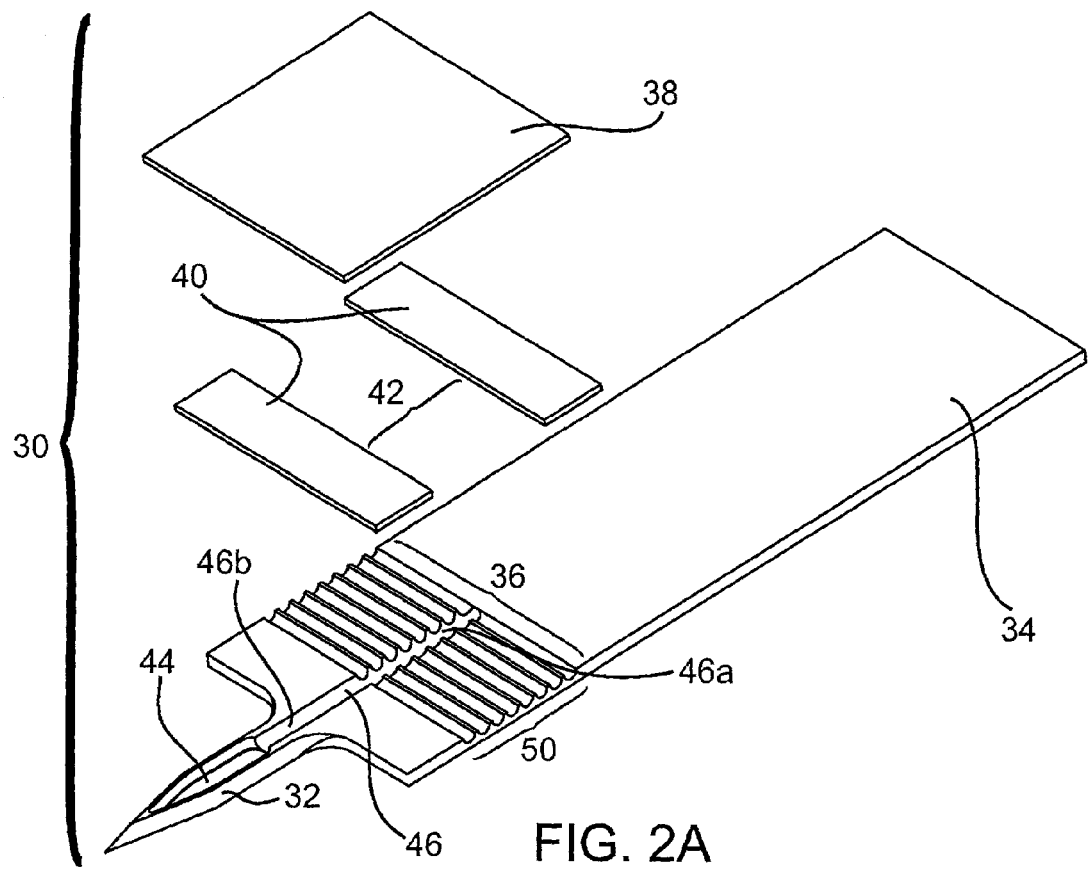
FIG. 2A is an exploded view of an embodiment of a colorimetric or photometric biosensor/skin-piercing/fluid access device suitable for use with the cartridge devices and systems of the present invention.

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a test strip" includes a plurality of such test strips and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in detail. In further describing the present invention, exemplary integrated biosensor/skin-piercing/fluid access devices suitable for use with the present invention are described first. Next, the subject systems and cartridge devices are described followed by a description of the various methods of using the subject systems and devices as well as methods for controlling the testing of physiological sample characteristics will then be described. Finally, a brief description is provided of the subject kits, which kits include the subject cartridges and/or systems for use in practicing the subject methods.

In the following description, the present invention will be described in the context of analyte concentration measurement applications; however, such is not intended to be limiting and those skilled in the art will appreciate that the subject devices, systems and methods are useful in the measurement of other physical and chemical characteristics of biological substances, e.g., blood coagulation time, blood cholesterol level, etc.

Exemplary Biosensor/Skin-Piercing/Fluid Access Devices

Various different embodiments of biosensor/skin-piercing/fluid access devices (also referred to herein as biosensor devices) may be employed with the present invention. Biosensor/skin-piercing/fluid access devices suitable for use with the present invention typically have a biosensor component in the form of a test strip or pad, such as an electrochemical, calorimetric or photometric test strip, and have a skin-piercing component in the form of a microneedle or a microlancet. Referring now to FIGS. 1A, 1B, 2A, 2B, 3, 4, 5A and 5B, there are shown such exemplary devices.

FIGS. 1A and 1B illustrate such an exemplary biosensor device 2 which is disclosed in the copending U.S. patent application Ser. No. 10/143,442, referenced above, herein incorporated by reference. Biosensor device 2 includes an electrochemical test strip configuration and a microneedle 6 integrated therewith. The biosensor is defined by an electrochemical cell generally having two spaced-apart and opposing electrodes 3 and 5, respectively referred to herein as bottom electrode 3 and top electrode 5. At least the surfaces of electrodes 3 and facing each other are comprised of a conductive layer 8 and 16, respectively, such as a metal, deposited on an inert substrate 4 and 18, respectively. The spacing between the two electrodes is a result of the presence of a spacer layer 12 positioned or sandwiched between electrodes 3 and 5. Spacer layer 12 preferably has double-sided adhesive to hold electrodes 3 and 5 together. Spacer layer 12 is configured or cut so as to provide a reaction zone or area 9. A redox reagent system or composition is present within reaction zone 9, and specifically selected to interact with targeted components in the fluid sample during an assay of the sample. The redox reagent system is deposited on the conductive layer of top electrode 5 wherein, when in a completely assembled form (shown in FIG. 1B), the redox reagent system resides within reaction zone 9. With such a configuration, bottom electrode 3 serves as a counter/reference electrode and top electrode 5 serves as the working electrode of the electrochemical cell. However, in other embodiments, depending on the voltage sequence applied to the cell, the role of the electrodes can be reversed such that bottom electrode 3 serves as a working electrode and top electrode 5 serves as a counter/reference electrode.

Microneedle 6 is integrally formed with and extends from and in the same plane as bottom electrode 3 and terminates distally in a sharp tapered tip 24 which facilitates penetration into the user's skin. Microneedle 6 further provides a space-defining configuration in the form of a concave recess 20 within its top surface. Such recess creates a corresponding space within skin tissue upon penetration of microneedle 6 into the skin. This space acts as a sample fluid collection reservoir or pooling area wherein fluid released upon penetration is pooled within the space prior to transfer into the electrochemical cell. Optionally, microneedle 6 may further include an opening 22 in fluid communication with recess 20 to facilitate the pooling rate of physiological fluid within the defined pooling area.

Biosensor device 2 further includes a sample fluid transfer or extraction pathway or channel 10 which extends from recess 20 to within the biosensor. At least a portion of the proximal end 10a of the pathway resides within the biosensor portion of device 2, specifically within reaction zone 9, and a portion of distal end 10b of pathway 10 resides within microneedle 6. Pathway 10 is dimensioned so as to exert a capillary force on fluid within the pooling area defined by recess 20, and draws or wicks physiological sample to within reaction zone 9. Extending laterally from proximal portion 10a of pathway 10 to within a portion or the entirety of the reaction zone 9 are sub-channels 15. Sub-channels 15 facilitate the filling of reaction zone 9 with the sampled fluid.

Figure 2B:
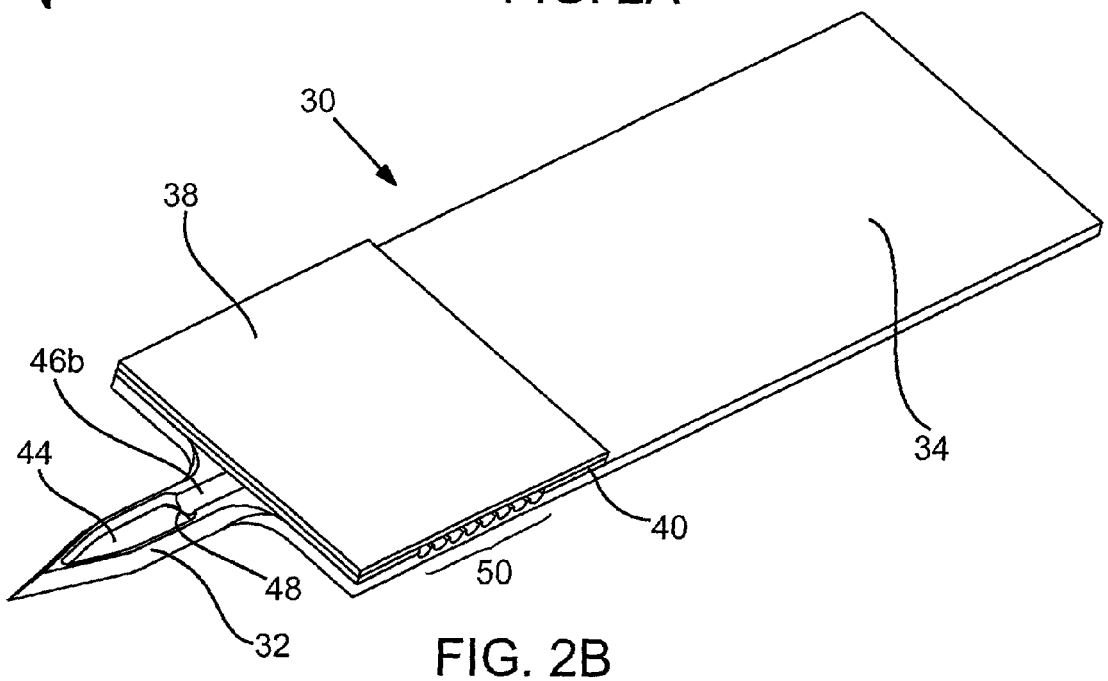
FIG. 2B is a perspective view of the assembled device of FIG. 2A

FIGS. 2A and 2B illustrate another suitable embodiment of a biosensor/skin-piercing/fluid access device 30 which is also disclosed in copending U.S. patent application 10/143,442. Device 30 has a photometric/colorimetric biosensor configuration and a microneedle 32 integrated therewith. The colorimetric or photometric biosensor is generally made up of at least the following components: a support element or substrate 34 made of either an inert material, such as plastic, or a metal material, a matrix area 36 for receiving a sample, a reagent composition (not shown as a structural component) within matrix area 36 that typically includes one or more members of an analyte oxidation signal producing system, an air venting port (not shown) and a top layer 38 which covers at least matrix 36. In other embodiments, top layer 38 may be a membrane containing a reagent composition impregnated therein while the matrix area 36 may or may not contain reagent composition. Further, test strip 30 has a double-sided adhesive layer 40 situated between substrate 34 and membrane 38 to hold them together. Double-sided adhesive layer 40 has a cut-out portion 42 which corresponds to the area covered by matrix 36 and defines an area for deposition of the sampled physiological fluid and for the various members of the signal producing system.

Microneedle 32 is formed with and extends from and in substantially the same plane as substrate 34 and has a space-defining configuration in the form of an opening 44 which extends transverse to a dimension, e.g., width or thickness, of microneedle 32. As with recess 20 of microneedle 6 above, opening 44 forms an open space within the tissue upon penetration of microneedle 32 into the skin. Such open space acts as a sample fluid collection reservoir wherein fluid released upon penetration is pooled within the space prior to transfer into the photometric/colorimetric cell.

Biosensor device 30 hosts a sample fluid transfer or extraction pathway 46 having a distal end 46b which extends within a portion of microneedle 32 and terminates at a distal opening 48. At least a portion of the proximal end 46a of pathway 46 resides within the biosensor portion of device 30, specifically within matrix area 36. Pathway 48 is dimensioned so as to exert a capillary force on fluid within the pooling area defined by opening 44, and draws or wicks physiological sample to within matrix area 36. Extending laterally from proximal portion 46a of pathway 46 to within a portion or the entirety of matrix area 36 are sub-channels 50, which facilitate the filling of matrix area 36 with the sampled fluid.

Figure 3:
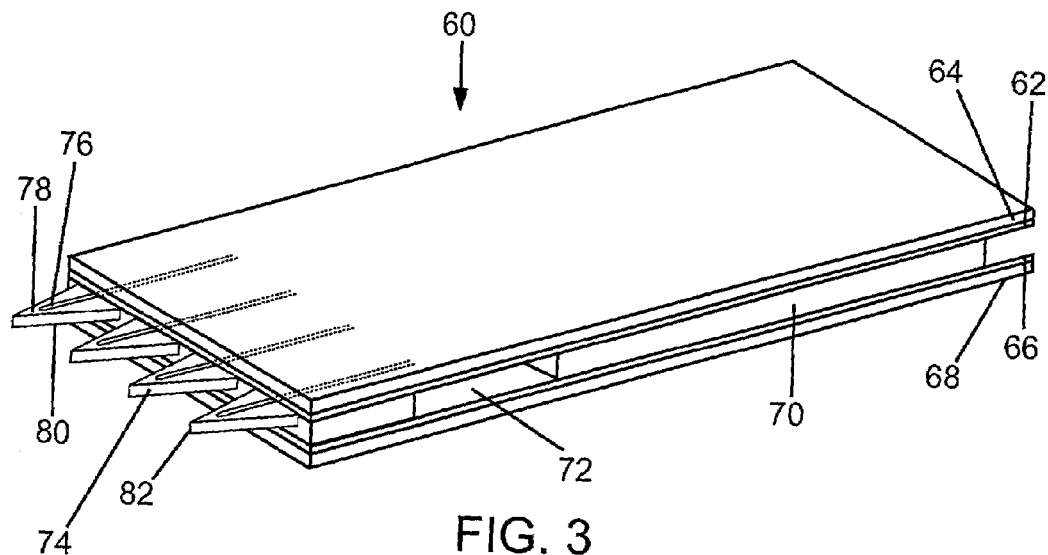
FIG. 3 illustrates yet another embodiment of an electrochemical biosensor/skin-piercing/fluid access device suitable for use with the cartridge devices and systems of the present invention.

FIG. 3 illustrates another exemplary biosensor device 60, disclosed in copending U.S. patent application Ser. No. 09/923,093, herein incorporated by reference, which is suitable for use with the present invention. Device 60 has an electrochemical test strip configuration similar to device 2 of FIGS. 1A and 1B, having a first electrode 62 with an associated inert substrate 64, a second electrode 66 with an associated inert substrate 68 and a spacer layer 70 there between which, collectively, form a reaction zone 72 having an appropriate redox reagent system. Instead of a single microneedle extending from an electrode or substrate thereof, as described with respect to the devices of FIGS. 1 and 2, device 60 has a plurality of skin-piercing elements 74 extending from and in substantially the same plane as spacer layer 70. Skin-piercing elements 74 may be made of the same material as spacer layer 70 or of a different material. Skin-piercing elements 74 each have a fluid channel 76 which extends proximally into spacer layer 70 to reaction zone 72. Each fluid channel 76 is open to the outside environment along a substantial length of a first side 78 and a second side 80 of the respective skin-piercing element and terminates proximal to distal tip 82 of the skin-piercing element 74. Channels 76 are dimensioned to exert a capillary force for collecting and transferring physiological sample accessed by the skin-piercing element 74. While each skin-piercing element is illustrated having a single fluid pathway 76, a plurality of such pathways may be used in each skin-piercing element 74.

Figure 4:
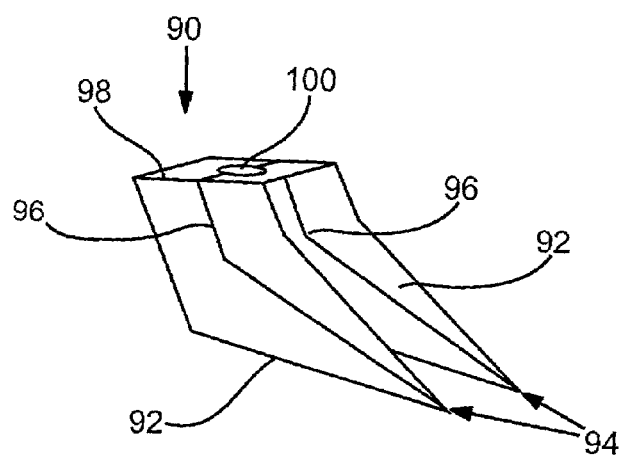
FIG. 4 illustrates another embodiment of an electrochemical biosensor/skin-piercing/fluid access device suitable for use with the cartridge devices and systems of the present invention.

FIG. 4 illustrates another suitable embodiment of a biosensor/skin-piercing/fluid access device 90 having an angled structure. Device 90 includes two piercing/fluid sampling microneedles 92, each including a flow pathway 96 extending from a distal opening 94 to a reaction zone or matrix area 100 of a proximal biosensor 98. The angled structures are typically elongated structures characterized by the presence of a single bend located proximal to the center of the elongated structure. The number of skin piercing structures, and thus the number of flow pathways, may vary, typically ranging from about 1 to 5, usually from about 1 to 4 and more usually from about 1 to 3, where the number of piercing elements typically ranges from 1 to 2 in many embodiments. The angle of the single bend typically ranges from about 135° to 150° and more usually from about 140° to 145°. The length from the bend to the very tip of the elongated angular structures typically ranges from about 2.3 to 3.2 μm and more usually from about 2.6 to 3.0.

The fluid flow pathways 96 have capillary dimensions that result in capillary flow of accessed physiological fluid from the distal openings 94 along the length of the flow pathway to the biosensor 98. As the flow path is one that has capillary dimensions, the flow path typically has a diameter at any point along its length in the range from about 80 to 150 µm. The flow path may be tubular or have some other configuration, e.g., one that provides for a cross-sectional shape that is a square, rectangle, oval, star, etc., where the configuration of the flow path is not critical so long as it provides for the desired capillary flow.

Biosensor 98 typically is made up of a sensor chamber that includes a transducing means which produces a signal in response to the presence, and typically concentration of, analyte in physiological fluid present in the chamber. The chamber located at the proximal end of device 90 typically has a volume in the range from about 100 to 300 µL. The transducing means may be any convenient transducing means that is capable of generating a signal in response to the presence of analyte in fluid present in the chamber. While in the broadest sense the transducing means may produce a signal that is indicative of the presence of analyte, in many preferred embodiments, the transducing means is one that generates a signal that is proportional to the amount of analyte in the physiological fluid.

One type of transducing means of interest that may be present in the subject sensors is a photometric transducing means. Photometric transducing means of interest typically include one or more reagents of a signal producing system that produces a detectable product in proportion to the amount of analyte present in the chamber. The detectable product is then photometrically detected to provide for a detection of the presence of analyte, and typically a measurement of the concentration of analyte, that is present in the fluid inside the chamber. Photometric transduction means of interest that may be employed in such biosensor devices include, but are not limited to, those described in U.S. Pat. Nos. 4,935,346; 5,049,487; 5,509,394; 5,179,005; 5,304,468; 5,426,032; 5,563,042; 5,843,692; and 5,968,760; the disclosures of which are herein incorporated by reference.

Another type of transducing means of interest that may be present in the subject sensors is an electrochemical transducing means. Electrochemical transducing means of interest typically include an electrochemical cell that includes two electrodes and one or more reagents of signal producing system, where these elements work in concert to produce an electrical current in proportion to the amount of analyte present in the chamber. The generated electrical current provides for a detection of the presence of analyte, and typically a measurement of the concentration of, analyte that is present in the fluid inside the chamber. Electrochemical transduction means of interest that may be employed in the biosensor devices include, but are not limited to, those described in U.S. Pat. Nos. 5,834,224; 5,942,102; and 5,972,199; as well as U.S. patent application Ser. Nos. 09/333,793; 09/497,269 and 09/497,304; the disclosures of which are herein incorporated by reference.

Figures 5A, 5B:
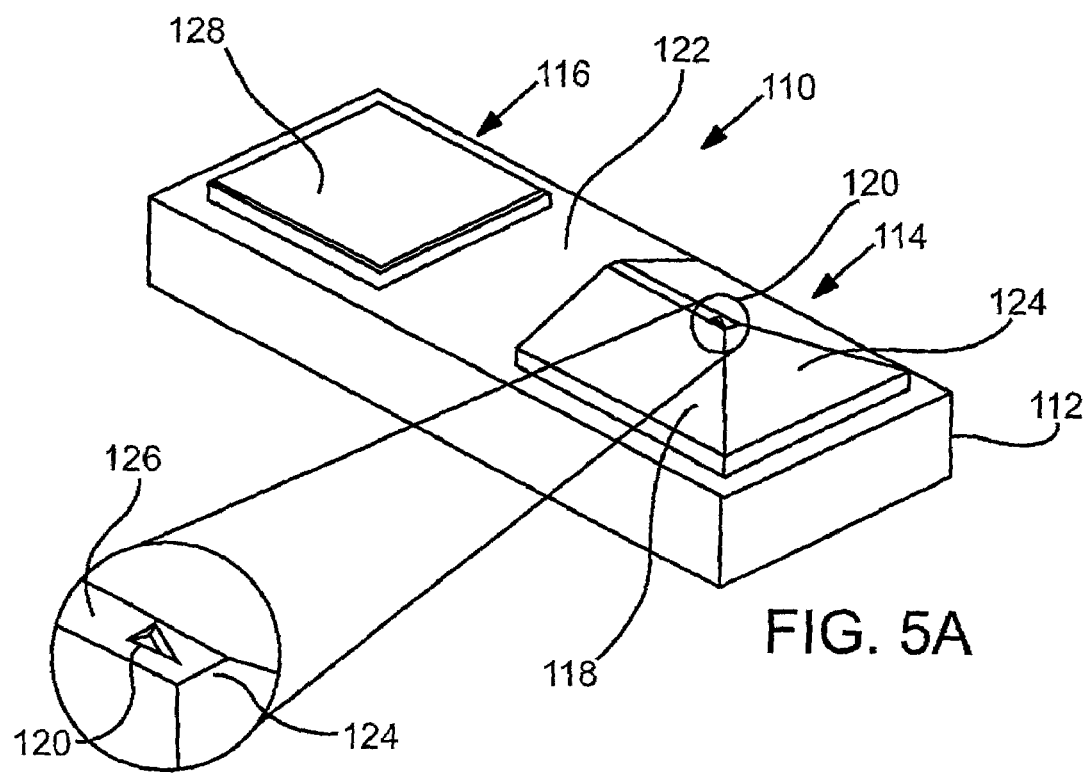
FIG. 5A illustrates another embodiment of a biosensor/skin-piercing/fluid access device suitable for use with the cartridge devices and systems of the present invention.
FIG. 5B is a magnified view of the skin-piercing element of the device of FIG. 5A.

FIGS. 5A and 5B illustrate another exemplary embodiment of a biosensor/skin-piercing/fluid access device 110 suitable for use with the present invention, which device is disclosed in the copending U.S. patent application Ser. No. 10/143,129, herein incorporated by reference. Device 110 includes a planar frame 112, and a blade portion 114 and a sensor portion 116 mounted on and carried by frame 112. Blade portion 114 includes an intermediate wedge or raiser member 118 upon which is mounted a blade or lancing element 120 which extends substantially transverse to planar frame 112. Member 118 serves to elevate blade or lancing element 120 relative to a skin-facing surface or face 122 of frame 112. Raiser member 118 has an angled front surface or ramp portion 124 which allows for smooth translational movement of device 110 relative to the skin of the user. A landing area 126 is provided upon which blade 120 is specifically mounted, the narrow construct of which acts to reduce frictional forces with the user's skin while increasing the ability to compress tissue riding over the structure. Blade 120 is provided with a triangular shape having a larger base and substantially vertical side portions, however, blade 120 may have any shape whose geometry is robust enough to avoid break-off. Sensor portion 116 is spaced apart from blade portion 114 to allow substantially flush engagement by sensor portion 116 with the cut area of the user's skin. Sensor portion 116 provides a sensor pad or area 128 for receiving the access physiological fluid, i.e., interstitial fluid or blood. Sensor pad 128 may have either an electrochemical or photometric configuration as described above.

While specific configurations of biosensor/skin-piercing/fluid access devices suitable for use with the systems of the present invention have been illustrated and described, it is understood that any type of biosensor, e.g., electrochemical, photometric, calorimetric, may be employed with one or more suitable skin-piercing elements or microneedles. Additionally, while specific shapes of skin-piercing elements and microneedles have been illustrated and described, any suitable shape of skin-piercing element may be employed with the biosensor devices, as long as the shape enables the skin to be pierced with minimal pain to the patient. For example, the skin-piercing element may have a substantially flat or planar configuration, or may be substantially cylindrical-like, wedge-like or triangular in shape such as a substantially flattened triangle-like configuration, blade-shaped, or have any other suitable shape. The cross-sectional shape of the skin-piercing element, or at least the portion of skin-piercing element that is penetrable into the skin, may be any suitable shape, including, but not limited to, substantially rectangular, oblong, square, oval, circular, diamond, triangular, star, etc. Additionally, the skin-piercing element may be tapered or may otherwise define a point or apex at its distal end. Such a configuration may take the form of an oblique angle at the tip or a pyramid or triangular shape or the like. The dimensions of the skin-piercing element may vary depending on a variety of factors such as the type of physiological sample to be obtained, the desired penetration depth and the thickness of the skin layers of the particular patient being tested. Generally, the skin-piercing element is constructed to provide skin-piercing and fluid extraction functions and, thus, is designed to be sufficiently robust to withstand insertion into and withdrawal from the skin.

In each embodiment, the biosensor/skin-piercing/fluid access devices are configured so as to provide a repeatable interface with the physiological fluid access site and with the target skin layer when operatively employed with the cartridge devices and systems of the present invention, which are now described in detail.

Systems of the Present Invention

Referring to FIGS. 6A, 6B, 6C and 6D, there is illustrated a physiological sample collection and measurement system 200 of the present invention having a compact, portable structural configuration. This structure includes an ergonomic housing 202 having a top portion 204 and a bottom portion 206 hinged together by hinge means 208 which allows top and bottom portions 204 and 206 to be opened apart and closed upon manual activation of depressible key 226 or the like. FIG. 6D illustrates housing 202 in such an open condition while FIGS. 6A, 6B and 6C illustrate housing 202 in a closed condition. Together, top housing portion 204 and bottom housing portion 206 define an interior compartment into which a cartridge device 210 of the present invention is operatively loaded and then removed after use. As will be described in greater detail below with respect to FIGS. 7A and 7B, cartridge 210 contains or provides one or more, and typically a plurality of, biosensor/fluid access devices 220.

When properly loaded within the interior compartment of the housing, the bottom surface of cartridge device 210 is positioned adjacent the internal side of a bottom wall 212 of bottom housing portion 206. Preferably, bottom wall 212 has an external surface configuration which is smooth and contoured as necessary to be flush against a selected area of the user's skin. Within bottom wall 212 is an aperture 214, as shown in FIG. 6C, sized and positioned such that a single biosensor/fluid access device 220 may be aligned with and exposed through aperture 214 while the remaining biosensor/fluid access devices 220 are concealed and protected within bottom wall 210. Associated with aperture 214 are contact means (not shown), e.g., electrical leads or an analogous means, for communicating electrical signals between device 220 when positioned at aperture 214 with a meter or measurement means (not shown) housed within housing 202. Such electrical signals include input signals from the meter to the device 220 for initiating the chemical reaction between a sampled fluid and a reagent within device 220 in order to determine a chemical characteristic, e.g., analyte (e.g., glucose) concentration, of fluid accessed and sampled from the user's skin by means of a device 220.

Such measurement means has the necessary construct and components for compatibility with the type of biosensor employed on devices 220, e.g., an electrochemical, photometric or colorimetric sensor. With an electrochemical based measurement system, the electrochemical measurement that is made may vary depending on the type of assay measurement and the meter employed, e.g., depending on whether the assay is coulometric, amperometric or potentiometric. Generally, the electrochemical measurement will measure charge (coulometric), current (amperometric) or potential (potentiometric), usually over a given period of time following sample introduction into the reaction area. Methods for making the above described electrochemical measurement are further described in U.S. Pat. Nos. 4,224,125; 4,545,382; and 5,266,179; as well as in International Patent Publications WO 97/18465 and WO 99/49307; the disclosures of which are herein incorporated by reference. With photometric/colorimetric assays, opticaltype meters are used to perform the assay. Such assays and methods and instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,773,452; 5,780,304; 5,789,255; 5,843,691; 5,846,486; 5,968,836 and 5,972,294; the disclosures of which are herein incorporated by reference.

System 200 further includes means for operatively moving cartridge 210 within housing 202 so as to operatively move cartridge 210 in order to sequentially position each biosensor/fluid access device 220 at or relative to aperture 214. Such cartridge movement involves advancement of cartridge 210 in one direction, e.g., clockwise, and reversal of cartridge 210 in the opposite direction, e.g., counter clockwise, relative to aperture 214 to align a device 220 within aperture 214 and to remove or conceal a device 220 from aperture 214. Such cartridge movement means may be a motor-driven system, or the like, or may be manually driven by the user by means of a ring or lever mechanism external to housing 202. In a motor-driven system, cartridge 210 may be provided with a drive wheel 232 such that, when cartridge device 210 is operatively loaded and positioned within housing 202, drive wheel 232 is engaged with a drive shaft 234 for rotating cartridge 210 in forward and reverse directions. Drive shaft 234 is in turn rotated by a drive motor, also located within compartment 230.

System 200 also includes biosensor movement means (not shown) associated with cartridge 210 at aperture 214 for applying a force on each device 220 that is positioned at aperture 214. Such biosensor movement means moves a device 220 downward from the bottom surface of the cartridge on which all of the devices 220 are positioned, and through aperture 214 so as to operatively contact device 220 with the selected skin area. Such operative contact involves piercing, cutting or lancing the skin surface with a skin-piercing element provided on each device 220. Any convenient means for applying such downward force on a device 220 may be employed, where representative means include spring means or analogous mechanical means, and the like, which are described in greater detail below.

System 200 further includes a controller having a microprocessor for controlling operation of the measurement means, data processing means, automated cartridge movement means, and a display 218 for displaying measurement data and other related data, e.g., to inform the user when all of the devices 220 have been used. The microprocessor may further be associated with a memory storage means for the short-term or long-term storage of measurement data. System 200 may further include a communication module for the bidirectional communication with a remote control device or and other devices, e.g., by wireless data communication means, e.g., telemetry means, such as by infrared (IR) transmission or radio frequency (RF) transmission, for the communication of assay protocol programs and information and for the immediate or later retrieval of measurement data and the like. System 200 further provides user control keys 224 on housing 202 to allow the user to enter or select data or parameters from menus displayed on the display, or to activate movement of the cartridge and an assay protocol, which representative data signals are sent to the system controller. System 200 may further control visual and audible alarms which alert the user when it is time for an assay to be performed, when a cartridge needs replacing, when an analyte measurement is outside of safe range, etc. A power supply and a battery are also provided to supply electrical power to the cartridge motor, the microprocessor and all components controlled by the microprocessor.

The system components just described may be housed in a protective, sealed compartment 230 wherein the necessary data or signal lines may run, for example, from compartment 230 in top housing portion 204 through hinge 208 to bottom housing portion 206. Alternately, such data or signal lines may be provided within top housing portion 204 such that they come into contact with corresponding data or signal lines within bottom housing portion 306 when the housing is in a closed condition.

Figure 7A:
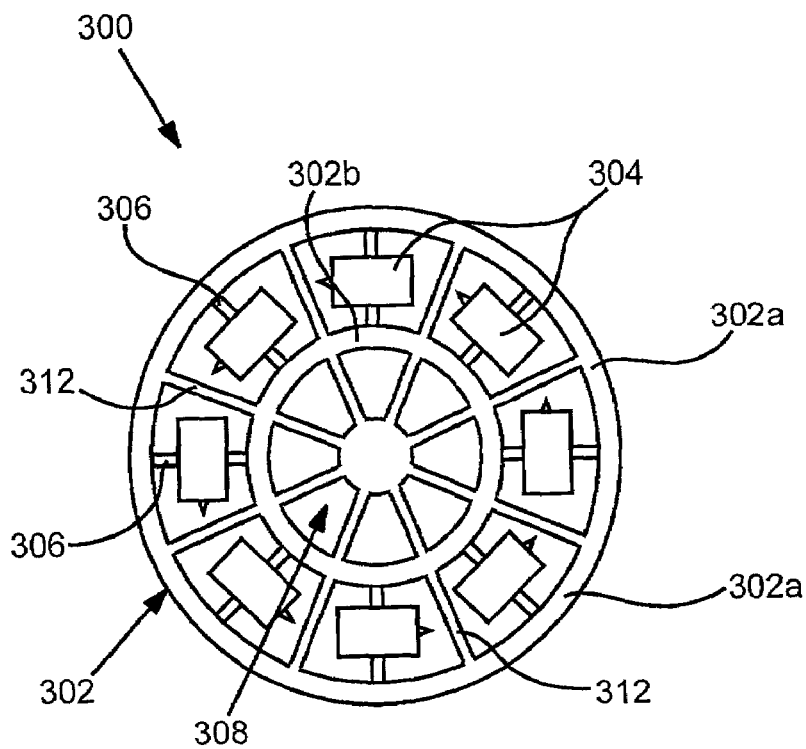
FIG. 7A is a schematic representation of one embodiment of a cartridge device of the present invention.

Referring now to FIG. 7A, there is shown a representation of one embodiment of a cartridge device 300 of the present invention suitable for use with at least the biosensor/skin-piercing/fluid access devices of FIGS. 1, 2 and 3. Cartridge device 300 has a cartridge body or frame 302 and a plurality of integrated biosensor/skin-piercing/fluid access devices 304 (also referred to herein as biosensor devices) positioned thereon, preferably in a serial arrangement wherein devices 304 are evenly spaced apart from each other. The cartridges of the present invention may host any suitable number of integrated biosensor devices 304 wherein the number of cartridges generally ranges from about 6 to 10.

In the annular or disk configuration of FIG. 7A, cartridge body 302 is defined by concentric frame rings, outer frame ring 302a and inner frame ring 302b. Rings 302a and 302b are fixed relative to each other by means of a plurality of torsion bars 306 which extend between rings 302a and 302b. Frame 304 is made of any rigid material such as injection molded plastic such as a polycarbonate material, while torsion bars 306 are preferably made of a material having properties and/or dimensions so as to be flexible or twistable about their longitudinal axis, e.g., stainless steel bars having a thickness in the range from about 50 to 75 µm and a width in the range from about 0.5 to 1 mm. Each integrated biosensor devices 304 is operatively attached to a torsion bar 306, preferably wherein there is a one-to-one correspondence between devices 304 and torsion bars 306. Each torsion bar 306 allows the corresponding attached device to rotate relative to frame 304 at least partially about the longitudinal axis defined by the torsion bar. As such, this axis of rotation is perpendicular to a path along which cartridge 300 is caused to rotate or travel. Cartridge 300 typically has a diameter ranging from about 3 to 4 cm, where the distance between the center of the disk and the biosensor devices typically ranges from about 7 to 9 mm.

As mentioned above, cartridge device 300 may further include a drive wheel 308 for attachment to a drive shaft housed within system 200 in which the cartridge device 300 is to be loaded. Alternatively, drive wheel 308 may also be separately housed within the system housing and be configured to receive and engage with cartridge frame 302. Drive wheel 308 includes a hub 310 and a plurality of frame bars 312 fixed to inner frame ring 302b. Rotation of drive wheel 308 causes rotational translation of cartridge body 302 and, thus, rotational translation of devices 304 about hub 310.

Figure 7B:
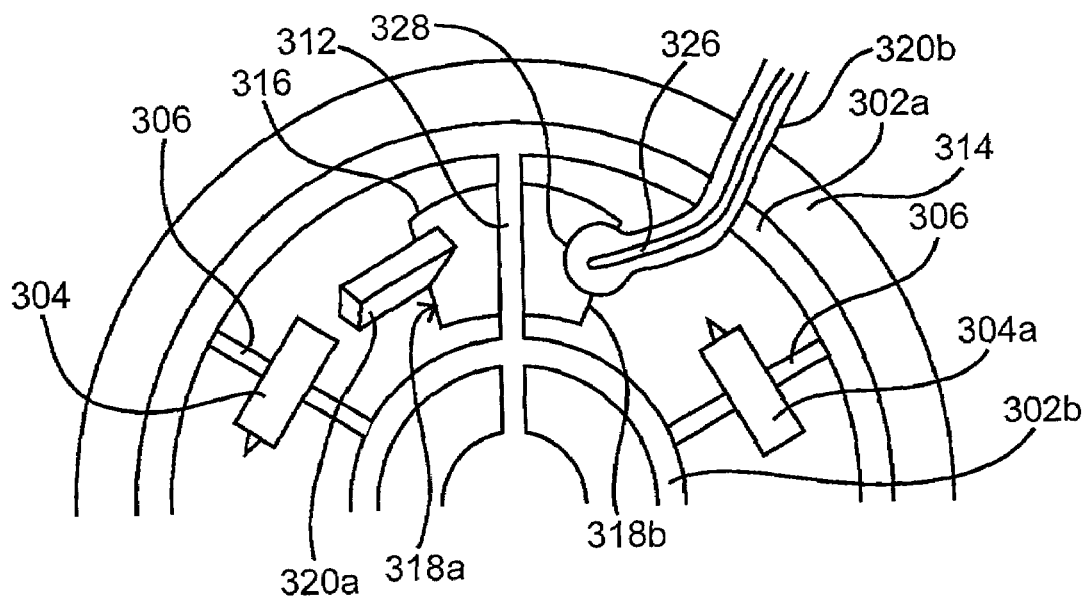
FIG. 7B is a view of an enlarged cut-away portion the cartridge device of FIG. 7A operatively engaged with a bottom portion of a system housing having an embodiment of a biosensor movement means of the present invention.

FIG. 7B illustrates a cut-away portion of cartridge device 300 operatively positioned within a bottom housing portion 314 of a subject system having an aperture 316. The width of aperture 316 is sufficient for the biosensor devices 316 to pass through, and typically ranges from about 3 to 8 mm and usually from about 4 to 6 mm. Components 320a and 320b of a biosensor movement means are operatively fixed within the system housing and located proximate a forward side 318a and a reverse side 318b of aperture 316, respectively. Component 320a has a wedged configuration and component 320b has a spring-loaded clip configuration. As best seen in FIGS. 8A–F, biosensor movement component 320a has a top planar surface 322 and a downward sloping front surface 324, while biosensor movement component 320b has a top clip member 326 spring-loaded or biased against a bottom clip member 328. Component 320a is positioned on bottom housing portion 314 and under cartridge device 300 while component 320b is positioned such that the plane in which cartridge device 300 and biosensor devices 304 rotate passes between clip members 326 and 328.

The movement undergone by a biosensor 304a throughout an assay application is now described with reference to FIGS. 8A–F. Cartridge device 300, when inactive, is preferably positioned such that aperture 316 is free and clear of biosensor devices 304 so as to prevent contamination of the biosensor devices and inadvertent injury to the user. Furthermore, each device 304 is maintained in a substantially planar position relative to bottom housing portion 314 by means of the tension placed on the devices 304 by torsion bars 306. Advancing or rotating cartridge device in the direction of arrow 330, i.e., in a counter clockwise direction with reference to FIG. 7B, will cause biosensor device 304a to advance or rotate in the same direction thereby approaching component 320b. As device 304a is advanced, it is caused to wedge between top clip 326 and bottom clip 328b (see FIG. 8A). As the clip members are biased against each other, biosensor device 304a is in frictional contact with component 320b when positioned between the clip members 326 and 328. When biosensor device 304a is sufficiently advanced in the direction of arrow 332 such that its back or proximal end 334 is between clip members 326 and 328, component 320b places a slight upward force or pressure on biosensor device 304a thereby causing device 304a to rotate about torsion bar 306 and front or needle end 336 of device 304a to deflect downward toward aperture 316 (see FIG. 8B). As device 304a is advanced further forward, in the direction of arrow 338, deflected front end 336 is caused to contact sloped front surface 324 of wedged component 320a (see FIG. 8C), thereby being further forced or deflected in a downward and forward direction. At this point, such deflection and forward motion is sufficient to cause the skin-piercing element 340 of device 304a to pierce the target skin surface of the user (not shown). During such piercing, physiological fluid, e.g., interstitial fluid or blood, is accessed and drawn up into the biosensor portion of device 304a for testing by the system's measurement componentry. After sufficient time for accessing and collecting a sample of physiological fluid has passed, the cartridge device 300 is caused to move in a reverse direction 342, e.g., in a clockwise direction, (see FIG. 8D) until device 304a becomes disengaged from movement components 320a and 320b and is caused by torsion bar 306 to return to its original planar position relative to cartridge rings 302a and 302b (see FIG. 8E). Finally, cartridge 300 is again advanced in a forward direction 346 until used device 304a completely passes over aperture 316 of FIG. 7B (see FIG. 8F), at which point cartridge 300 may be locked in place so as to prevent inadvertent movement and possible injury to the user. Such process is repeated with each device 304 when an assay protocol is activated by the user. When all devices 304 are used, i.e., have been employed to perform an assay protocol, the used cartridge may be removed from the system's housing and properly disposed of. A replacement cartridge may then be loaded into the system.

Referring now to FIGS. 9A–9G, there is shown another embodiment of a biosensor movement means 400, particularly suited for use with the biosensor/skin-piercing/access devices of FIG. 4. The biosensor movement means 400 includes spaced-apart components 402a and 402b present within the housing of the subject systems. Components 402a and 402b are spaced apart so as to straddle an aperture 401 within the bottom housing wall, as described above, and provide surfaces and edges to guide a biosensor device 404 through aperture 401 for operatively contacting a target skin surface area of a user. Such surfaces and edges match the slope of the surfaces and the angles of the edges of biosensor device 404. More specifically, component 402a has an angled surface 410 that matches the back surface 412 of angled biosensor device 404. Angled surface 410 typically forms an angle α with the bottom surface 414 of component 402a that ranges from about 40° to 55°, and more usually from about 45° to 50°. Furthermore, component 402b has a top surface 406 that engages a bottom surface 408 of the angled biosensor device 404, and has an angled back surface 416 that matches a front surface 418 of angled biosensor device 404. Angled back surface 416 typically forms an angle β with the bottom surface 420 of component 402b that ranges from about 30° to 50° and more usually from about 25° to 35°.

Figure 9A:
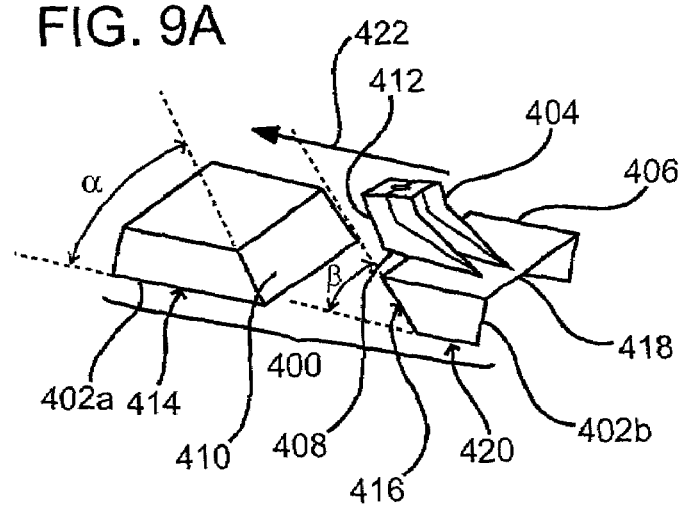
FIGS. 9A to 9G provide a schematic representation of another embodiment of a biosensor movement means of a system of the present invention and the step-by-step movement of a biosensor/skin-piercing/fluid access device of FIG. 4 on a cartridge of the present invention.
Figure 9B:
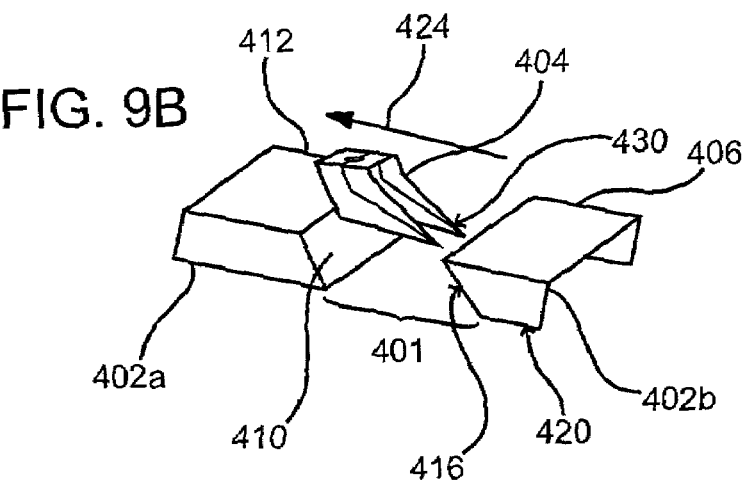
Figure 9C:
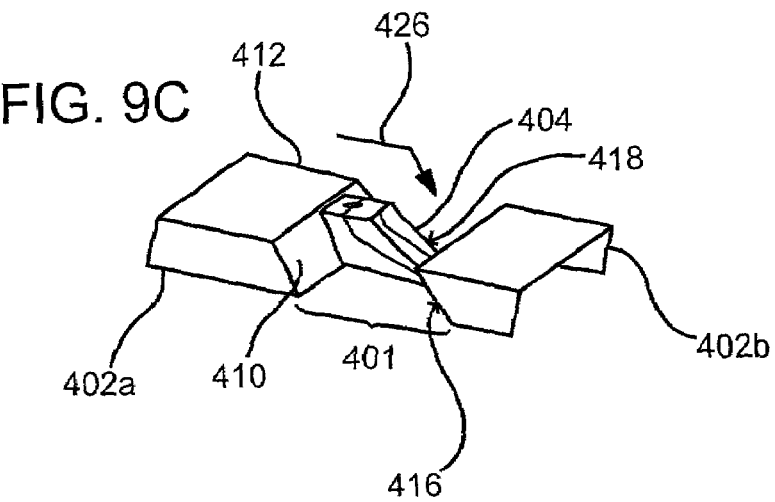
Figure 9D:
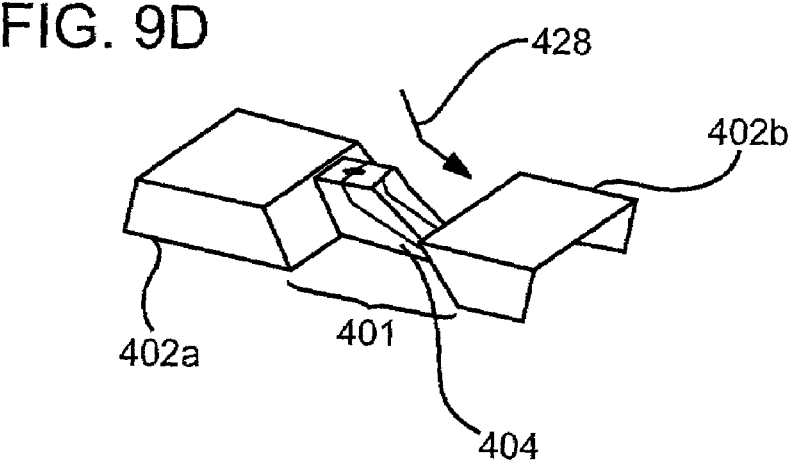

The movement undergone by biosensor device 404 throughout an assay application is now described with reference to FIGS. 9A–9G. As with the embodiment described with respect to FIGS. 7A and 7B, biosensor device 404 may be operatively attached to a cartridge (not shown) by way of a tension bar (not shown) or by way of a rotational pivot attachment to a hub/spoke (see FIGS. 10A–10C) such that biosensor device 404 is held in an original biased position in which bottom surface 408 of device 404 is flush with top surface 406 of component 402b. In FIG. 9A, angled biosensor 404 is moved in a first direction according to arrow 422, across top surface 406 of component 402b. FIG. 9B shows that as the angled biosensor 404 is moved across the spacing between components 402a and 402b in the direction of arrow 424, it drops down into the opening there between, moving along sloped surface 410 of component 402a. At this point, the direction of travel of angled biosensor 404 is reversed, as shown in FIG. 9C, in the forward direction indicated by arrow 426. Because of the downward force applied by the cartridge, angled biosensor 404 continues to move downward along sloped surface 410 such that bottom surface 408 of angled biosensor 404 becomes flush with a targeted skin surface exposed through aperture 401. Continued forward movement of angled sensor 10, in the direction of arrow 428 (see FIG. 9D), brings front surface 418 of angled biosensor 404 into contact with inversely sloped surface 416 of component 402b. This contact forces biosensor 404 further downward and into the skin surface to the target skin surface, causing the skin-piercing configurations 430 of biosensor 404 to penetrate the target skin surface to selected skin layer, e.g., the dermis, epidermis, subdermis, etc., thereby accessing the physiological fluid of interest, e.g., interstitial fluid or blood, which fills the capillary flow path of biosensor 404.

Figure 9E:
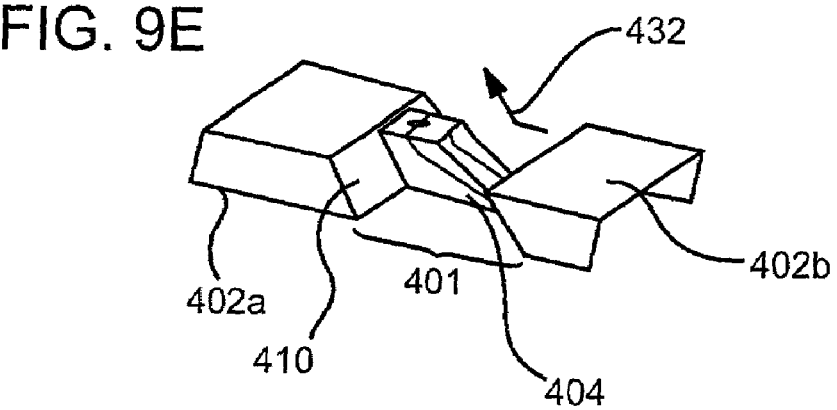
Figure 9F:
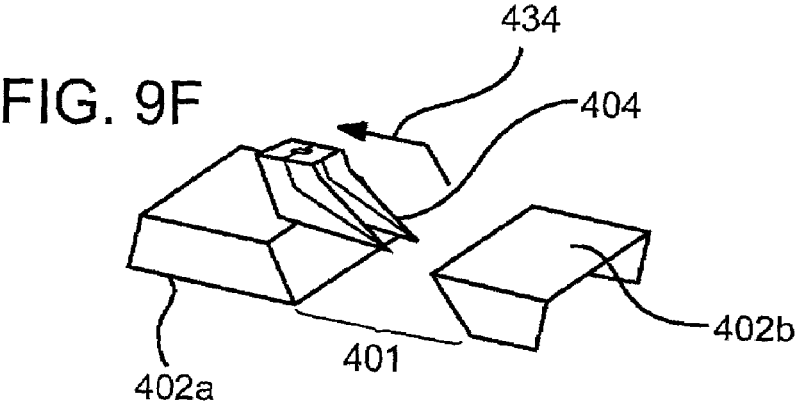
Figure 9G:
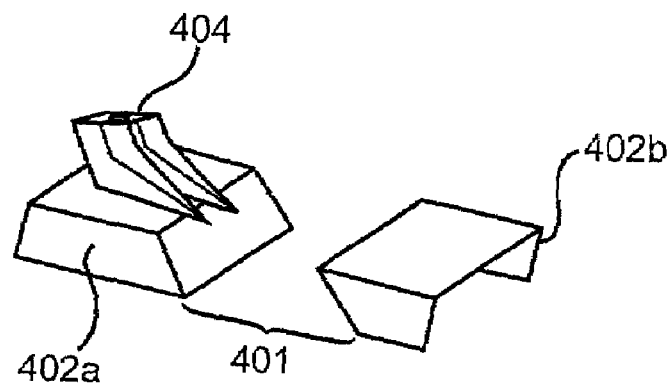

Following sampling and fluid fill of the capillary flow path of biosensor 404, biosensor 404 is again moved in the first direction as shown in FIG. 9E according to arrow 432. Continued movement of biosensor 404 in the first, reverse direction causes removal of biosensor 404 from the skin surface/sampling site and brings biosensor 404 up, out of the opening between components 402a and 402b, as shown in FIG. 9F and indicated by arrow 434. Once the angled sensor is brought out of the opening, as shown in FIG. 9G, the fluid present in the biosensor chamber can be assayed. (Of course, where desired the fluid can be assayed while the sensor is still in situ, depending on the preferred sampling/measurement protocol being employed.) Such process is repeated with each biosensor device 404 when an assay protocol is activated by the user. When all devices 404 are used, i.e., have been employed to perform an assay protocol, the used cartridge may be removed from the system's housing and properly disposed of. A replacement cartridge may then be loaded into the system.

Figure 10A:
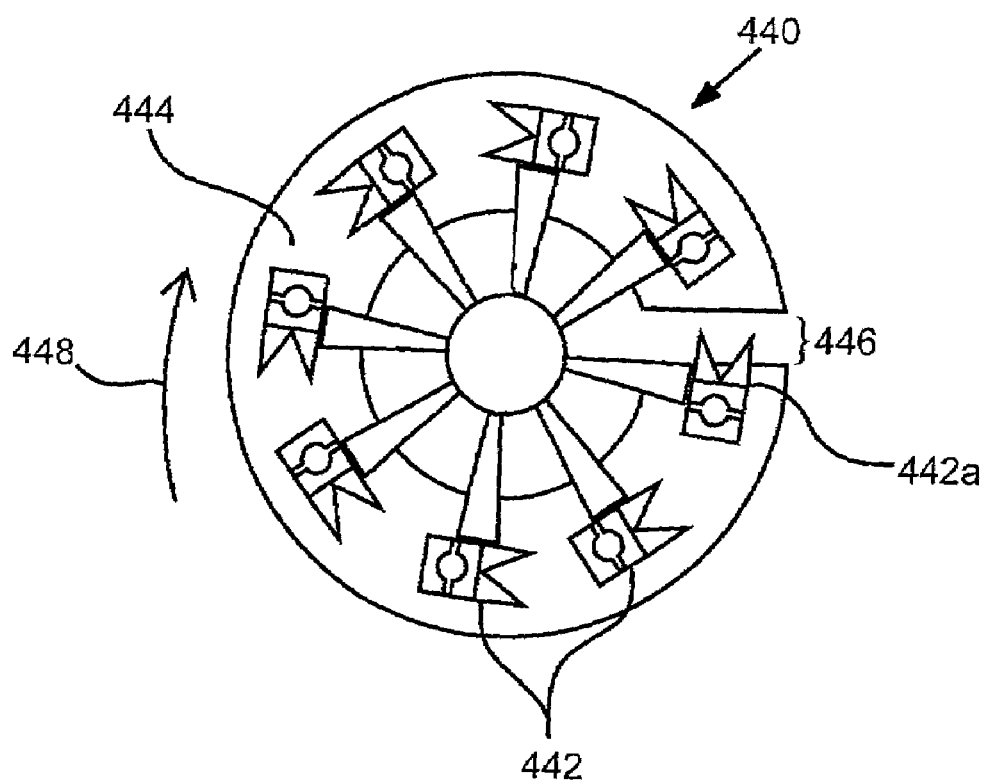
FIGS. 10A to 10C provide a schematic representation of the step-by-step movement of a cartridge of the present invention employed with the biosensor/skin-piercing/fluid access device of FIG. 4.
Figure 10B:
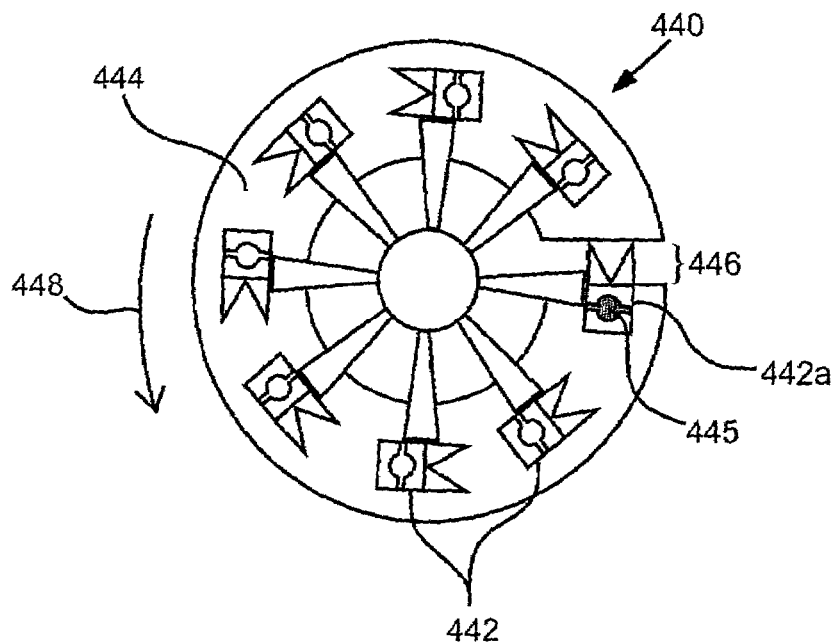
Figure 10C:
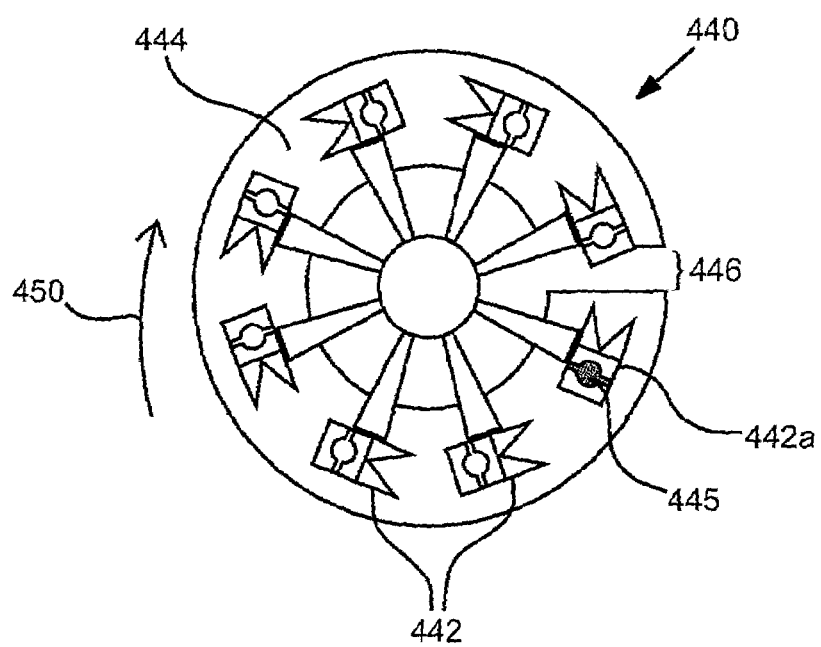

The cartridge movement means of the embodiment described with respect to FIGS. 4 and 9 is further illustrated in terms of a representative rotary cartridge device as shown in FIGS. 10A to 10C. In FIG. 10A, rotary or disk cartridge 440 includes 8 individual angled biosensors 442 and is positioned on top of bottom surface 444 of housing (not shown) having an aperture 446 therein. In use, cartridge 440 rotates in a first clockwise direction 448 as shown in FIG. 10A to operatively position a biosensor 442 relative to the biosensor movement means according to FIGS. 9A and 9B. The direction of the cartridge rotation is then reversed to a counter-clockwise direction 450 as shown in FIG. 10B, which brings the biosensor 442a into the aperture 446 within bottom surface 444 wherein the target skin surface area is pierced and physiological fluid is accessed an transported to the chamber of biosensor 442a. Then, the direction of rotation of cartridge 440 is again reversed to a clockwise direction 452 as shown in FIG. 10C, which withdraws biosensor 442a out of the skin, followed by subsequent measurement of analyte in the accessed fluid.

With minor modifications understood by those skilled in the art, the biosensor configuration described above with respect to FIG. 5 may be similarly employed with the cartridge embodiments of FIGS. 7 and 8 or of FIGS. 9 and 10 and their respective cartridge and biosensor movement means. As such, the cartridge as well as the corresponding construct of the subject system may be configured in a number of different ways, so long as the cartridge device can be manipulated in a forward and reverse direction for performing the assay protocol, and as along as the biosensor devices can be operatively manipulated the biosensor movement means of the system so that the biosensor devices present on the cartridge can pierce the skin surface and access the physiological fluid therein.

The device and systems may take a variety of different configurations. In certain embodiments, the devices are single integral devices, in which the measurement means, processing means, display means etc. are all present on the same structure. In yet other embodiments, one or more of the components may be separate from the other components. For example, the measurement means may be separated from the display means, where telemetric communication or analysis data transmission means, e.g., radio frequency or RF means, are employed to provide for data communication between the two or more disparate components of the device.

Figure 11A:
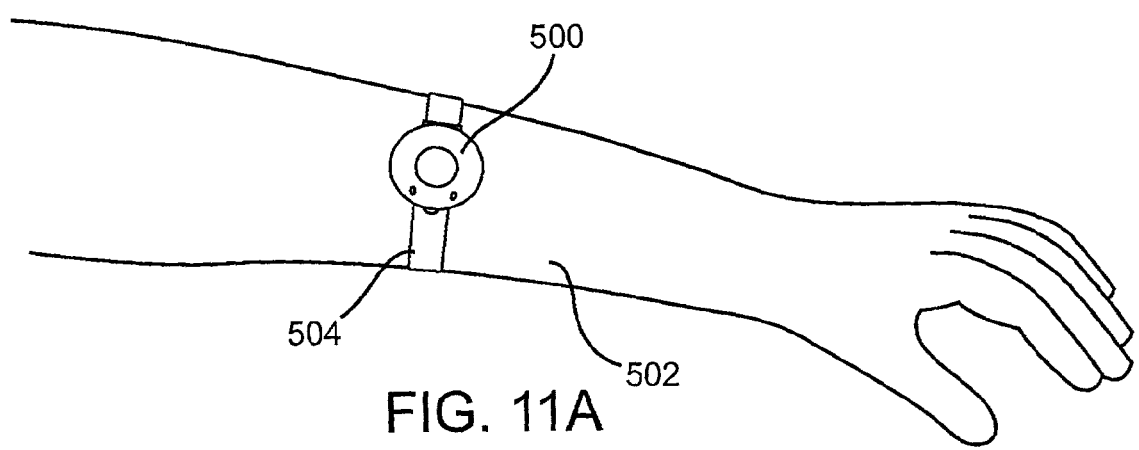
FIG. 11A illustrates "wristband" embodiment of the subject system.
Figure 11B:
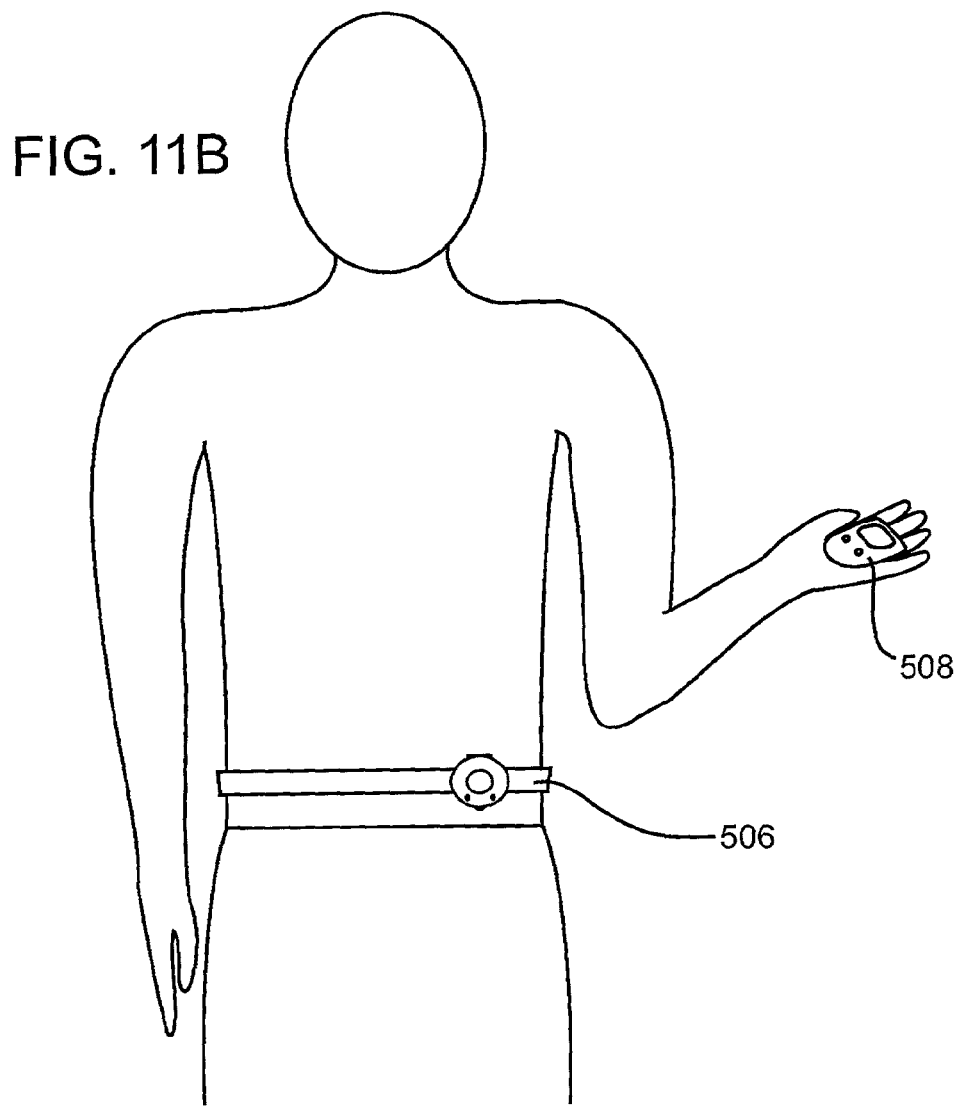
FIG. 11B illustrates a "waistband" embodiment of the subject system which is used with and in communication with a remote control device.

One representative subject system embodiment is a "watchband" embodiment as shown in FIG. 11A, in which the device 500 is configured to be worn around a limbic portion 502, e.g., a forearm, in a manner analogous to a watch. In this embodiment, all of the components of the device may be present in one integral unit, where the unit is maintained in contact with the skin of the host via an adjustable strap 504 or other retention means.

Where it is desirable to have a subject system in contact with a portion of the user that is not readily viewable, e.g., a portion of the waste or other portion that is typically covered by clothes or otherwise not readily viewable, a two component system, as shown in FIG. 11B, may be employed. With such an embodiment, the cartridge device and measurement means, i.e., the biosensors and meter, are present within one component, e.g., a "waistband" component 506, and the display and control means are present on a second component of the system, e.g., a hand-held, remote control unit 508. The two components communicate with each other a data communication means, where the data communication means is typically a wireless data communication means, e.g., RF telemetric means.

In other embodiments of the present invention, the subject systems do not require a band or strap for attachment, but instead, may be attached to an appropriate skin area by means of a biocompatible adhesive.

Methods of the Present Invention

The subject systems and devices find use in methods of determining a characteristic of physiological fluid, most typically, measuring the concentration of an analyte in a physiological fluid. In practicing the subject methods, a device having an integrated biosensor and skin-piercing element, such as the various embodiments described above, is provided and positioned relative to a target skin surface area of the user. The integrated biosensor device is caused to move or translate from an initial or retracted position to a second, extended or skin-contacting position skin wherein the target surface is pierced, and physiological fluid is accessed and transported to the biosensor portion of the device. The translation or movement of the device is reversed to remove and retract it from the skin.

When used with the subject cartridge devices described above, a plurality of such integrated biosensor devices is provided in operative engagement with the cartridge device. The cartridge device is provided and positioned planar to a target skin surface area of the user. A movement means is employed to move or translate the cartridge in a first direction which acts to move or translate the biosensor device from an initial or retracted position to a second, extended or skin-contacting position wherein the target surface is pierced, physiological fluid is accessed and transported to the biosensor portion of the device. The movement means is then activated to move or translate the cartridge device in a second or reverse direction which acts to move or translate the biosensor from this second, extended position back to a retracted position. Such movement of the biosensor device from a retracted to a skin-contacting position, and visa versa, may be further defined by deflecting the biosensor device from a substantially planar position to angled or deflected position for contacting and piercing the skin.

When used with the subject system as described above, the cartridge device is provided within or loaded into a housing structure having a skin-facing wall having an aperture therein. The external surface of the skin-facing wall is preferably positioned flush with the targeted skin surface area of the user. The cartridge device is positioned within housing structure such that it is planar with the skin facing surface and wherein the translation of the plurality of biosensor devices is in a pathway directly over the aperture. Upon movement or translation of the cartridge as described above, the movement or deflection of a particular biosensor device involves passage of at least the skin-piercing element through the aperture to contact and pierce the skin surface.

The subject methods further include providing a meter or measurement means as described above in operative contact with the biosensor device for measuring the selected characteristic of the sampled physiological fluid transferred to the biosensor device upon accessing the physiological fluid. Upon filling of the reaction zone or matrix area of the biosensor device with the sampled physiological fluid, a signal is applied to the biosensor by the meter componentry of the subject system, and the chemical characteristic of interest, e.g., analyte concentration, is made and the resulting measurement data is displayed via a display provided on the system housing and is stored into memory for immediate or later retrieval.

The subject methods, devices and systems find use in a variety of different applications in which detection of an analyte and/or measurement of analyte concentration in a physiological fluid is desired. The subject systems, devices and methods find particular use in analyte concentration monitoring applications over a given period of time, as described in copending U.S. patent application Ser. No. 09/865,826, the disclosure of which is herein incorporated by reference, where the physiological fluid sampling/measurement occurs automatically and continuously according to a predetermined schedule.

In these monitoring applications, the present invention may be employed to: (a) continuously monitor an analyte whose concentration is associated with a disease condition, e.g., hypo-or hyperglycemia in blood sugar disorders such as diabetes; (b) continuously monitor an analyte whose concentration is associated with a non-disease physiological condition of interest, e.g., alcohol intoxication, illegal drug use; (c) continuously monitor the concentration of a therapeutic agent in drug therapy applications; etc.

Where the analyte is glucose, the present invention finds use in a variety of different applications relating to the treatment and management of glucose associated disease conditions, e.g., diabetes and related conditions. In these embodiments, the subject methods and devices find use in providing for "continual" glucose monitoring, by which is meant that glucose levels in a patient are measured intermittently and automatically according to a predetermined schedule. The subject methods can also be employed to detect and predict the occurrence of hypo- and hyperglycemic conditions. In such applications, the pattern of continually monitored analyte concentration measurements can be employed to determine whether a patient is experiencing hyper- or hypoglycemia by comparing the pattern of measurement results stored within the systems memory storage means to a control or reference pattern. In addition, one can look at a pattern of measurements and compare it to an appropriate control or reference pattern to predict the occurrence of a hypo or hyperglycemic condition. The subject methods can be part of a more comprehensive therapy protocol designed to prevent the occurrence of hypo and hyperglycemic events, e.g., by predicting the occurrence of such events with the subject methods and device and intervening in blood sugar metabolism in a manner that prevents the occurrence of the predicted event.

The present invention may be employed with a variety of different types of hosts where analyte monitoring is desired. Hosts of interest include, but are not limited to mammals. Mammals of interest include valuable livestock, e.g., horses, cows, sheeps, etc., pets, e.g., dogs, cats etc., and humans. In most embodiments, the mammals on which the subject methods are practiced are humans.

Kits

Also provided are kits for practicing the subject methods. In one embodiment, the kits include a system for practicing the subject invention. The system may be a single integral device or made up of two or more disparate components, e.g., a remote-control and display component and a measurement component. The kits may include a single disposable cartridge device, or two or more disposable cartridges devices, as described above for use with the subject system. Finally, the kits typically include instructions for using the subject systems and for loading and removing cartridges into and out of the subject system. These instructions may be present on one or more of the packaging, a label insert, containers present in the kits, and the like.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A system comprising:
a plurality of devices wherein each said device comprises:
   (i) a skin-piercing member configured to access physiological fluid beneath the skin surface;
   (ii) a biosensor for measuring a characteristic of the accessed physiological fluid wherein said skin-piercing member is integrated with said biosensor; and
   (iii) a physiological fluid transfer pathway extending from said at least one skin-piercing member to said biosensor; and
wherein the hosuing comprises at least one ramped surface for deflecting said skin-piercing member through the skin surface at an oblique angle relative to said skin surface when said skin-piercing member is operatively positioned relative to said skin surface; and
means for moving each of said plurality of devices in a manner that provides for cooperation between said at least one ramped surface and said skin-piercing member to cause penetration of the skin surface by said skin-piercing member at said oblique angle relative to the skin surface by said skin-piercing member.

2. The system according to claim 1 wherein each said device comprises a planar configuration wherein said skin-piercing member extends therefrom.

3. The system according to claim 2 wherein said skin-piercing member extends substantially within the same plane as said planar configuration.

4. The system according to claim 3 wherein said planar device defines a biosensor having a test strip configuration and said skin-piercing member extends from said test strip.

5. The system according to claim 2 wherein said skin-piercing member extends in a direction substantially transverse to said planar device.

6. The system according to claim 5 wherein said planar device defines a frame having a biosensor portion and a skin-piercing portion spaced apart from each other.

7. The system according to claim 1 wherein each said device comprises an angled configuration having a distal end defining said skin-piercing member and a proximal end defining said biosensor.

8. The system according to claim 1 wherein said biosensor comprises an electrochemical configuration.

9. The system according to claim 1 wherein said biosensor comprises a photometric configuration.

10. The system of claim 1, wherein said plurality of devices is provided in a cartridge.

11. the cartridge according to claim 10 further comprising a frame and a plurality of torsion bars attached to said frame wherein each said device is operatively attached to a torsion bar.

12. The cartridge according to claim 11 wherein each said torsion bar allows said attached device to be movable relative to said frame.

13. The cartridge according to claim 12 wherein each said torsion bar allows said attached device to rotate at least partially about an axis defined by said torsion bar.

14. The cartridge according to claim 13 wherein said axis of rotation is perpendicular to a path along which said cartridge is caused to travel.

15. The cartridge according to claim 10 wherein said cartridge comprises a disk configuration and wherein said serial arrangement of said plurality of devices is about a circumference of said cartridge.

16. A method for accessing a physiological fluid sample of a host for measuring the concentration of an analyte with said physiological fluid, said method comprising the steps of:
   (a) providing the system according to claim 10 in planar apposition to a skin surface of said host;
   (b) moving said cartridge in a first direction wherein said skin-piercing member of one of said plurality of devices is caused to penetrate into said skin surface at an oblique angle relative to the skin surface thereby accessing physiological fluid and wherein physiological fluid is transferred by means of said fluid transfer pathway to said biosnesor; and
   (c) moving said cartridge in a reverse direction thereby removing said skin-piercing member from said skin surface.

17. The method according to claim 16, further comprising repeating steps (b) and (c) for each device of said plurality of devices.

18. The method according to claim 17, wherein said step of repeating occurs according to a predefined time schedule.

19. A system comprising:
a housing structure having a skin-facing portion and an aperture within said skin-facing portion;
a cartridge receivable within said housing structure and comprising a plurality of devices, each said device comprising a sensor means for measuring a characteristic of a physiological fluid, a skin-piercing element and a physiological fluid transfer pathway extending from said skin-piercing element and said sensor means;
means for moving said cartridge within said housing structure so as to operatively position each of said plurality of devices relative to said aperture;
at least one ramped surface for deflecting said skin-piercing element through said aperture when one of said devices is operatively positioned relative to said aperture; and
a meter housed within said housing structure for applying signals to said sensor means for measuring a characteristic of physiological fluid and for receiving signals from said sensor means.

20. The system according to claim 19, wherein said means for moving said cartridge moves each of said devices relative to said aperture in a forward and then in a reverse direction.

21. The system according to claim 19, wherein said means for moving said cartridge provides for rotational movement of said cartridge.

22. The system according to claim 19, wherein said means for moving said cartridge comprises motor-driven means.

23. The system according to claim 19, further comprising means for controlling the movement of and the timing of said movement of said cartridge.

24. The system according to claim 19, further comprising means for processing signals received by said meter.

25. The system according to claim 19, further comprising a display means in said housing structure.

26. The system according to claim 19, wherein said housing structure is configured to be worn on a limbic region.

27. The system according to claim 19, wherein said housing structure is configured to be worn about the waist.

28. The system according to claim 19, wherein said aperture is sized to expose only a single device at a time.

29. A method for accessing a physiological fluid sample of a host for measuring the concentration of an analyte within said physiological fluid, said method comprising the steps of:
- (a) providing the system according to claim 11 wherein said skin-facing portion of said housing structure is in contact with a section of the user's skin surface;
- (b) moving said cartridge in a first direction wherein said device proximate said aperture within said skin-facing portion of said housing structure is caused to move relative to said cartridge such that said skin-piercing element of said device is caused to penetrate into said skin surface thereby accessing physiological fluid and wherein physiological fluid is transferred by means of said fluid transfer pathway to said biosensor; and
- (c) moving said cartridge in a reverse direction thereby removing said skin-piercing member from said skin surface.

30. The method according to claim 29, further comprising repeating steps (b) and (c) for each device of said plurality of devices.

31. The method according to claim 30, wherein said step of repeating occurs according to a predefined time schedule.

32. The method according to claim 29, further comprising the step of measuring said analyte concentration.

33. The method according to claim 32, further comprising the step of displaying said analyte concentration following said measurement.

34. A kit for use in determining the concentration of at least one analyte within a sample of physiological fluid, said kit comprising:
- a system according to claim 19; and
- at least two of said cartridges, wherein said cartridges are disposable.

35. The kit according to claim 34, further comprising instructions for using said system.

36. The kit according to claim 35, wherein said system is configured for application to a portion of a user's torso.

37. The kit according to claim 34 wherein said system is configured for application to a portion of a user's arm.

38. The kit according to claim 37 wherein said system further comprises a strap for securing said housing structure to the user's arm.

39. the kit according to claim 36, wherein said system further comprises an adhesive for adhering said housing structure to the user's torso.

40. A system comprising:
- a housing structure having a skin-facing portion and an aperture within said skin-facing portion;
- a cartridge receivable within said housing structure and comprising a plurality of devices, each said device comprising a sensor means for measuring a characteristic of a physiological fluid, a skin-piercing element and a physiological fluid transfer pathway extending from said skin-piercing element and said sensor means;
- means for moving said cartridge within said housing structure so as to operatively position each of said plurality of devices relative to said aperture;
- means for deflecting said skin-piercing element through said aperture when one of said devices is operatively positioned relative to said aperture, said deflection means comprising a clip mechanism; and
- a meter housed within said housing structure for applying signals to said sensor means for measuring a characteristic of physiological fluid and for receiving signals from said sensor means.

\* \* \* \* \*